US009537473B2

(12) United States Patent
Winokur et al.

(10) Patent No.: US 9,537,473 B2
(45) Date of Patent: Jan. 3, 2017

(54) DIGITALLY ASSISTED ANALOG DYNAMIC RANGE ENHANCER

(71) Applicants: Massachusetts Institute of Technology, Cambridge, MA (US); Analog Devices, Inc., Norwood, MA (US)

(72) Inventors: Eric Steven Winokur, Danvers, MA (US); Charles G. Sodini, Belmont, MA (US); Tom O'Dwyer, Arlington, MA (US)

(73) Assignees: Massachusetts Institute of Technology, Cambridge, MA (US); Analog Devices, Inc., Norwood, MA (US)

( * ) Notice: Subject to any disclaimer, the term of this patent is extended or adjusted under 35 U.S.C. 154(b) by 422 days.

(21) Appl. No.: 14/320,994

(22) Filed: Jul. 1, 2014

(65) Prior Publication Data

US 2015/0257708 A1    Sep. 17, 2015

Related U.S. Application Data

(60) Provisional application No. 61/952,623, filed on Mar. 13, 2014.

(51) Int. Cl.
*A61B 5/02* (2006.01)
*H03K 5/1252* (2006.01)
*A61B 5/024* (2006.01)
*A61B 5/00* (2006.01)

(52) U.S. Cl.
CPC ......... *H03K 5/1252* (2013.01); *A61B 5/02427* (2013.01); *A61B 5/7225* (2013.01)

(58) Field of Classification Search
CPC .. A61B 5/02427; A61B 5/7225; H03K 5/1252
See application file for complete search history.

(56) References Cited

PUBLICATIONS

Patterson et al., "Dual-Mode Additive Noise Rejection in Wearable Photoplethysmography," IEEE 2012 Ninth International Conference on Wearable and Implantable Body Sensor Networks, 2012, pp. 97-102.
Wong et al., "A 0.5-Hz High-Pass Cutoff Dual-Loop Transimpedance Amplifier for Wearable NIR Sensing Device," IEEE Transactions on Circuits and Systems—II: Express Briefs, vol. 57, No. 7, Jul. 2010, pp. 531-535.

*Primary Examiner* — Mark Remaly
(74) *Attorney, Agent, or Firm* — K&L Gates LLP

(57) ABSTRACT

A circuit for expanding a dynamic range. In one embodiment, the circuit includes: a transducer generating a signal current on an output terminal in response to a physical quantity, the signal current comprising an AC current and a DC current; a dynamic range enhancement circuit having a digital control signal input terminal and producing a variable opposition current in response to a digital signal applied to the digital control signal input terminal; an amplifier; an analog to digital converter in electrical communication with the amplifier; and a digital feedback circuit in communication with the output terminal of the analog to digital converter and in electrical communication with the digital control signal input terminal of the dynamic range enhancement circuit, wherein the opposition current from the dynamic range enhancement circuit is set substantially equal to the DC current portion of the signal current from the transducer.

19 Claims, 5 Drawing Sheets

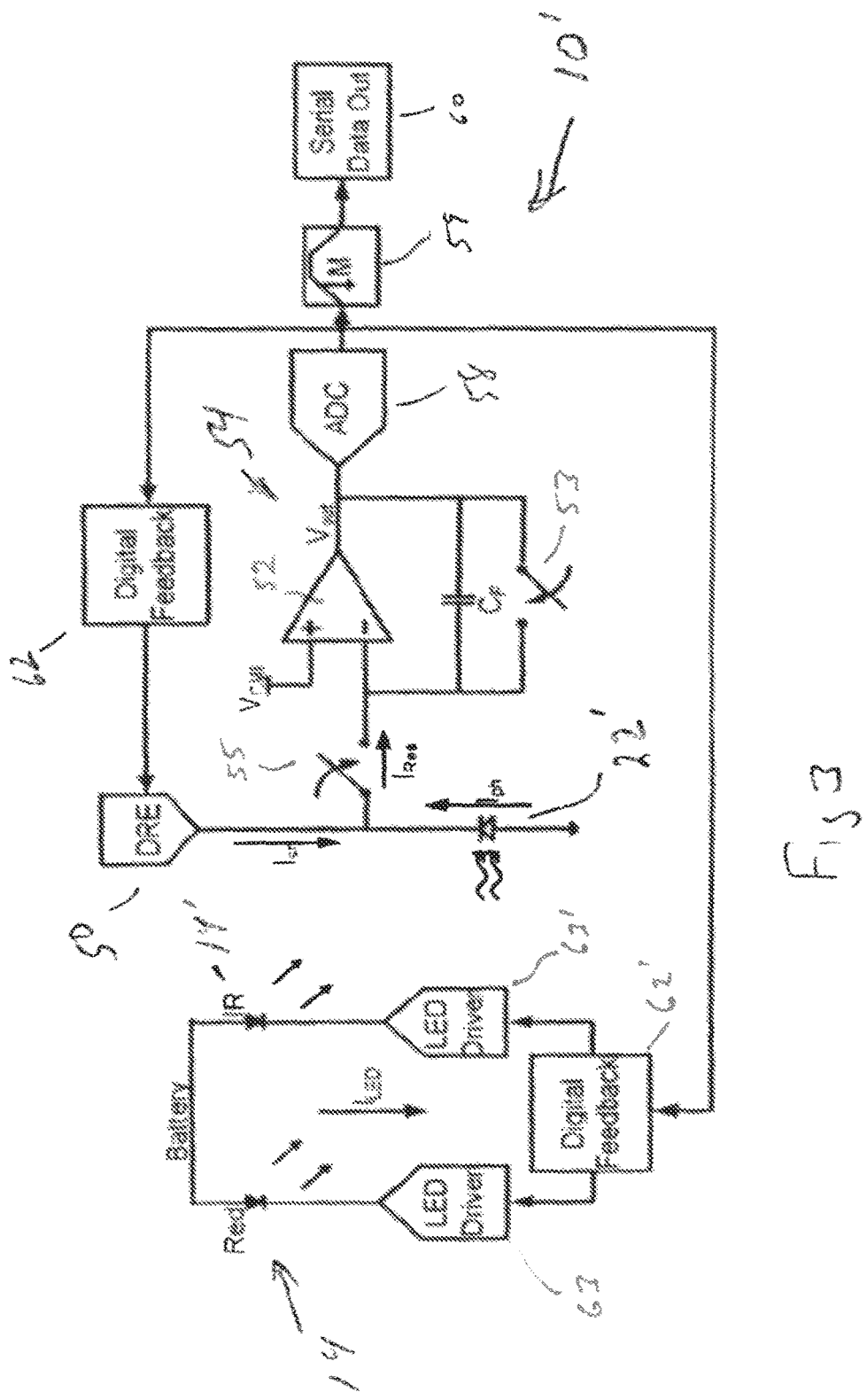

DIGITALLY ASSISTED ANALOG DYNAMIC RANGE ENHANCER

RELATED APPLICATIONS

This application claims priority to U.S. Provisional Application 61/952,623 filed Mar. 13, 2014, which is herein incorporated by reference.

FIELD OF THE INVENTION

The invention relates generally to signal processing, and more specifically to extending the dynamic range of a signal.

BACKGROUND OF THE INVENTION

Low amplitude signals are frequently obscured by the noise generated by a sensor of the signal. Thus, small changes in the actual signal are masked. One way around this problem is to extend the dynamic range of the signal by amplification.

One such signal having a small change in amplitude relative to the underlying background signal is generated by photoplethysmography (PPG) measurements. In these measurements, light is used to measure the changes in vascular blood volume generally in a peripheral part of the body. The volume of blood in that body part, such as a finger, changes during each heartbeat.

In a typical embodiment of a photoplethysmographic system 10 (FIG. 1), light from a light source 14, such as a light emitting diode 14, is either transmitted through or reflected from the internal vasculature (only through shown for clarity) and detected by a photodetector 22. Generally the light source 14 actually comprises a red LED and an InfraRed (IR) LED (not shown). The signal from the photodetector 22 is amplified by an amplifier 24, demodulated by demodulator 26 so that the signals from the red and IR LEDs can be separated, low-pass filtered 28, and converted to digital form by an analog-to-digital converter 30. The digitized signal is processed by a microprocessor 32 and the PPG measurements displayed by an output device 34. The microprocessor also determines when the LED lights 14 should be turned on and controls the illumination using an LED driver circuit 36. The electrical signal from the photodetector varies over the heart beat cycle and is analyzed by the processor using signal processing techniques.

One way known to the prior art to increase the dynamic range of the signal from the photodetector is shown in FIG. 2. This embodiment involves using an analog error amplifier 40 in a feedback loop with a main amplifier 44 and photodiode 38. This error amplifier 40 controls a transistor 42 which generates a current that cancels the static current of the photodiode 38. The error amplifier 40 tries to maintain the output of the main amplifier 44 at a specific voltage that is typically at the midsupply voltage of the system. The pass-band of the circuit is dependent upon the amount of current sourced by the transistor. Because PPG signals are typically low frequency, it is difficult to generate a pole close enough to DC in an integrated circuit to make the pass band of the circuit begin at 1 Hz. Thus, these systems frequently infringe on the bandwidth of interest and are inherently lossy.

What is needed is a system that permits expanded dynamic range while having components that permit it to be constructed in a small package such as an integrated circuit for portable use.

SUMMARY OF THE INVENTION

In one aspect, the invention relates to a circuit for expanding a dynamic range. In one embodiment, the circuit includes a transducer generating a signal current on an output terminal in response to a physical quantity, the signal current comprising an AC current and a DC current; a dynamic range enhancement circuit having a digital control signal input terminal and producing a variable opposition current at an output terminal in response to a digital signal applied to the digital control signal input terminal, the output terminal of the dynamic range enhancement circuit being in electrical communication with the transducer output terminal; an amplifier having a input terminal and an output terminal, the input terminal of the amplifier in electrical communication with the output terminal of the dynamic range enhancement circuit and the transducer output terminal; an analog to digital converter having an input terminal in electrical communication with the output terminal of the amplifier and having an output terminal; and a digital feedback circuit having an input terminal in electrical communication with the output terminal of the analog to digital converter and having an output terminal in electrical communication with the digital control signal input terminal of the dynamic range enhancement circuit, wherein the opposition current from the dynamic range enhancement circuit is set substantially equal to the DC current portion of the signal current from the transducer by the digital feedback circuit in response to the difference between DC current portion of the signal current and the opposition current. In another embodiment, the transducer is a photodetector. In yet another embodiment, the transducer is a photodiode. In still yet another embodiment, the amplifier is configured as a switched integrator. In another embodiment, the amplifier is configured as a resistive transimpedance amplifier.

In another aspect, the invention relates to a photoplethysmograph circuit with an expanded dynamic range. In one embodiment, the photoplethysmograph circuit includes a receiver portion including a transducer generating a signal current on an output terminal in response to a physical quantity, the signal current comprising an AC current and a DC current; a dynamic range enhancement circuit having a digital control signal input terminal and producing a variable opposition current at an output terminal in response to a digital signal applied to the digital control signal input terminal, the output terminal of the dynamic range enhancement circuit being in electrical communication with the transducer output terminal; an amplifier having a input terminal and an output terminal, the input terminal of the amplifier in electrical communication with the output terminal of the dynamic range enhancement circuit and the transducer output terminal; an analog to digital converter having an input terminal in electrical communication with the output terminal of the amplifier and having an output terminal; and a digital feedback circuit having an input terminal in electrical communication with the output terminal of the analog to digital converter and having an output terminal in electrical communication with the digital control signal input terminal of the dynamic range enhancement circuit, wherein the opposition current from the dynamic range enhancement circuit is set substantially equal to the DC current portion of the signal current from the transducer by the digital feedback circuit in response to the difference between DC current portion of the signal current and the opposition current; and a light source portion comprising: one or more light sources, each with a different wavelength; and an intensity control in electrical communication with each light source, wherein the intensity control is adjusted to pulse each light source; and wherein the light source is positioned such that at least some fraction of the light transmitted from the light source is received by the transducer.

In another embodiment, the transducer is a photodetector. In yet another embodiment, the photodetector is a photodiode. In still yet another embodiment, the light source is a light emitting diode. In one embodiment, the light received by the transducer from the light source is light transmitted through a bodily tissue. In another embodiment, the light received by the transducer from the light source is light reflected by a bodily tissue. In yet another embodiment, the amplifier is configured as a switch integrator. In another embodiment, the amplifier is configured as a resistive transimpedance amplifier.

In another aspect, the invention relates to a dynamic range enhancement circuit. In one embodiment, the circuit includes a clock generating two non-overlapping clock output signals; a variable capacitor having a ground terminal in electrical communication with ground, a control terminal which controls the capacitance of the variable capacitor, and an input terminal; a first switch, including an input terminal in communication with a voltage source, a control terminal in electrical communication with one of the non-overlapping clock output signals, and an output terminal in electrical communication with the input terminal of the variable capacitor; a second switch, comprising an output terminal, a control terminal in electrical communication with the other of the non-overlapping clock output signals, and an input terminal in electrical communication with the output terminal of the first switch and in electrical communication with the input terminal of the variable capacitor, wherein the first clock signal causes the first switch to connect the input terminal of the variable capacitor to the voltage source, and wherein the second clock signal causes the second switch to connect the input terminal of the variable capacitor to a current sink.

BRIEF DESCRIPTION OF THE DIAGRAMS

FIG. 3 is a schematic diagram of an embodiment of a dynamic range enhancer circuit using an integrator constructed in accordance with the invention;

DESCRIPTION OF A PREFERRED EMBODIMENT

Figure 1:
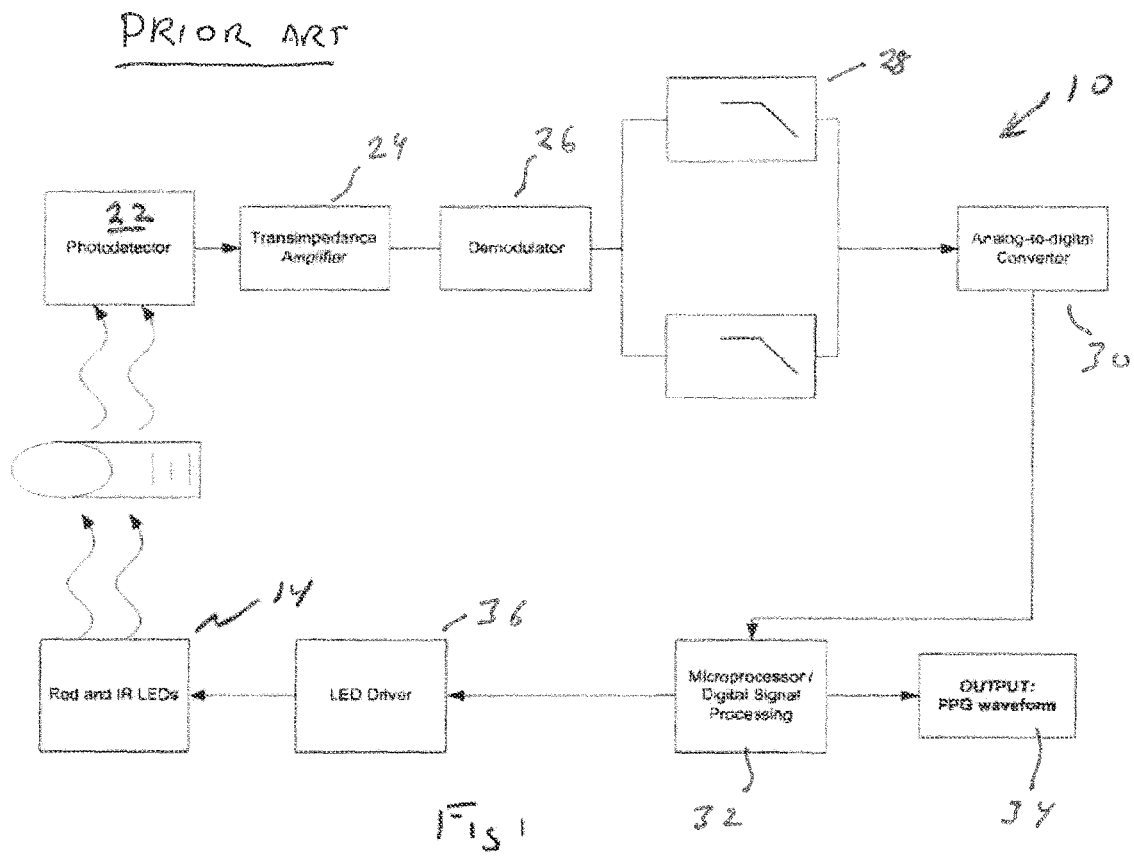
FIG. 1 is a schematic diagram of photoplethysmograph circuit known to the prior art.

A digitally assisted dynamic range enhancer is a circuit type and technique that can be used to separate static and time varying signals from a sensor. This is particularly important when the static component is much larger than the time varying component. Referring to FIG. 3, the device shown may be used in a photoplethysmogram (PPG) front end 10', which comprises the dynamic range enhancer circuit 50, a photodiode 22', and an integrating transimpedance (main) amplifier 54. In the configuration shown, photoplethysmogram signals typically have static or DC components that are 25× to 400× larger than their time varying components. For such a use, it is desirable to design the circuit such that it may be constructed as a small package such as an integrated circuit.

In more detail, when the two LEDs 14, 14' (in one embodiment, red and IR respectively) are turned on, the photodiode 22' generates a photocurrent $I_{ph}$. In other embodiments, other wavelengths and other numbers of LEDs are used. The dynamic range enhancer 50 is also turned on, which generates a current $I_{st}$ in the opposite direction to the photodiode current $I_{ph}$. The resulting remaining current, $I_{Res}$ equal to $(I_{ph}-I_{st})$, is integrated by the amplifier 52, as part of a switched integrator 54, and the resulting output of the switched integrator is digitized by an A/D converter or ADC 58. Amplifier 54, in one embodiment, is a switched integrator topology. In this arrangement, when the circuit is not integrating, termed the first configuration, the reset switch 53 is closed and the $I_{Res}$ switch 55 is open. Once the LEDs 14, 14' turn on, typically sequentially, the reset switch 53 opens and the $I_{Res}$ switch 55 closes to integrate the signal, termed the second configuration. The switches remain in the second configuration until the A/D 58 has sampled the output of the switched integrator 54, at which time the switches return to the first configuration. In one embodiment, the output of the A/D converter is decimated 59 by a factor of M and is output 60 as data. The output of the A/D converter also is fed back to the dynamic range enhancer 50 and the LED drivers 63, 63' respectively, through digital feedback modules 62'. In another embodiment, only one LED driver 63 is used and the output of the driver is switched to control both LEDs. The digital feedback modules 62, 62' are integrated processing circuits executing the algorithm of FIG. 4, as explained below.

Using this technique allows the amplifier gain to be much larger than typical, while being powered by a low voltage supply. This is because the amplifier 52 is not being saturated by the large static component of the input signal. The current of the dynamic range enhancer 50 is set in digital steps by the digital feedback module 62 so that the output of the system is within the power supply rails of the amplifier 52.

Figure 3A:
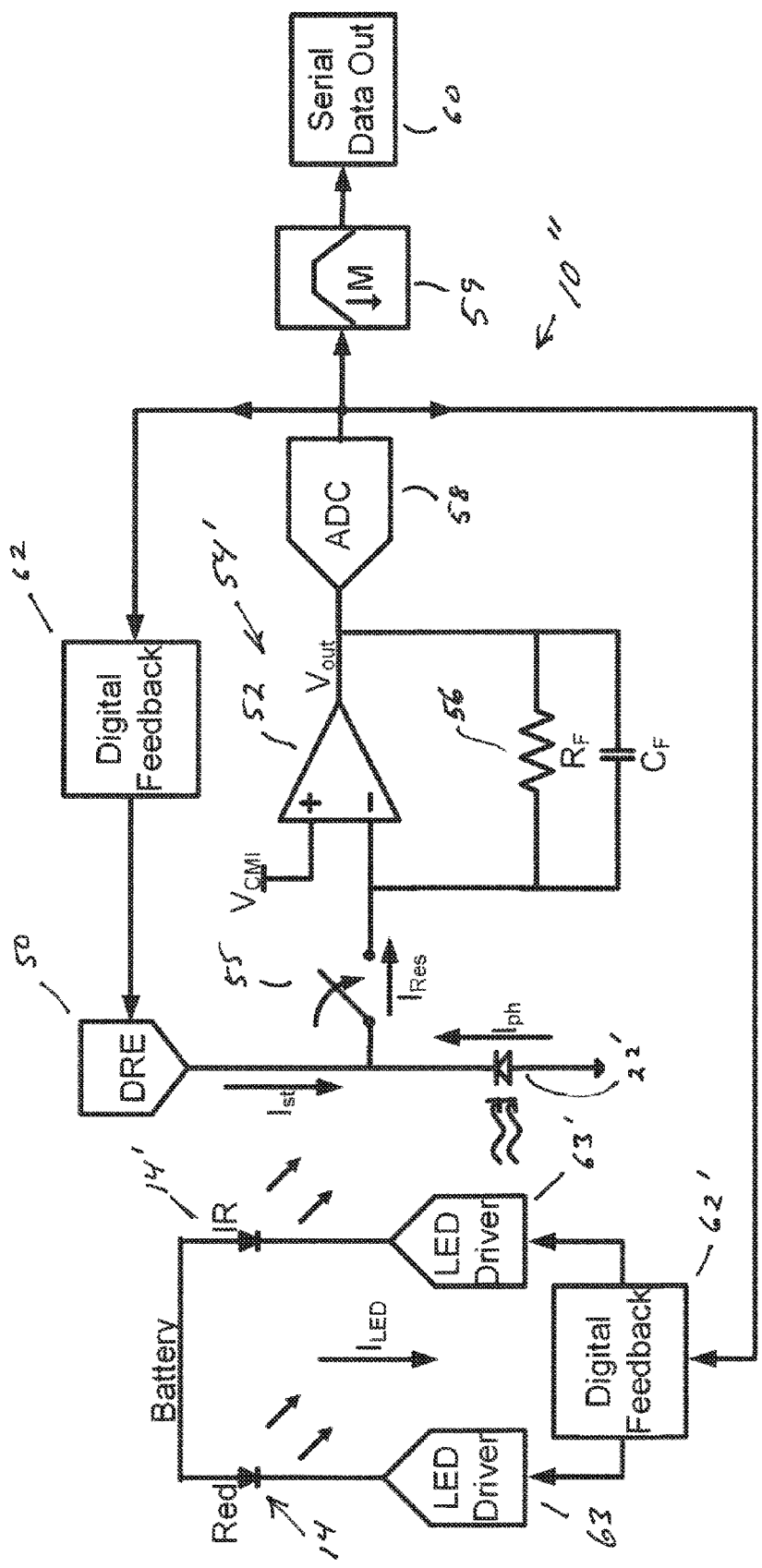
FIG. 3(a) is a schematic diagram of another embodiment of a dynamic range enhancer circuit using a resistive transimpedance amplifier constructed in accordance with the invention.

Referring to FIG. 3(a), in another embodiment the switched integrator 54 (FIG. 3) is replaced with a resistive transimpedance amplifier configuration 54'. In this embodiment, output of the transimpedance amplifier 52 is connected to one of its inputs through a resistor 56, instead of switch 53 (FIG. 3).

Figure 4:
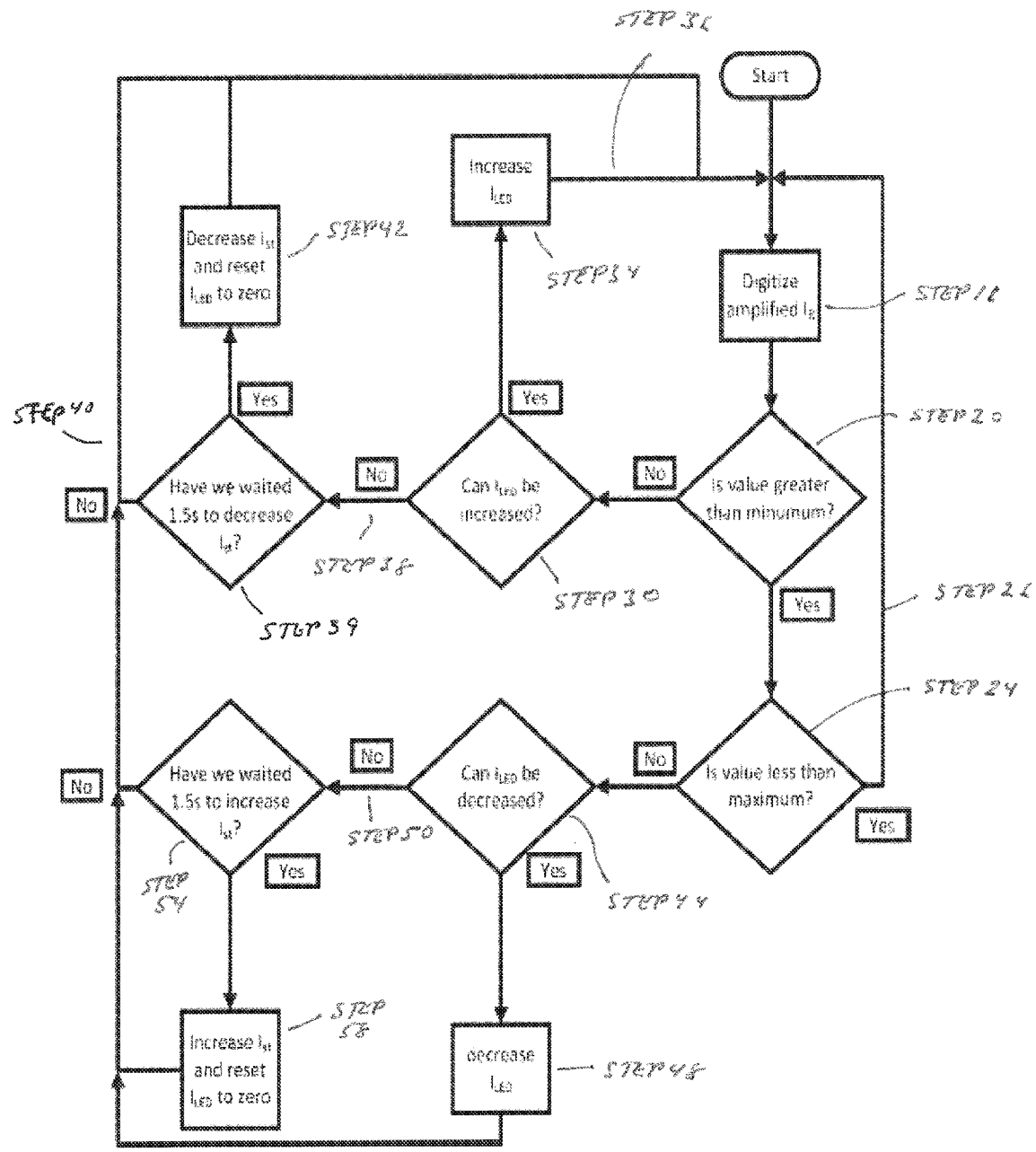
FIG. 4 is a flow diagram of an embodiment of the control of the current in the circuit of FIGS. 3 and 3(a)

In operation, and referring to FIGS. 3, 3(a) and 4, if the digitized output $V_{out}$ of the amplifier 54 (Step 16) is greater than a minimum threshold (Step 20), and less than a maximum threshold (Step 24), then the digital feedback 62, 62' will not change either $I_{st}$ or $I_{LED}$, respectively, and the algorithm loops to obtain the next value (Step 26). If, however, $V_{out}$ is below a minimum threshold (Step 20), the algorithm determines if the LED current $I_{LED}$ can be increased (Step 30). If it can, then the feedback 62 will increase $I_{LED}$ (Step 34) and loop for the next sample (Step 36). If $I_{LED}$ is already at a maximum (Step 38), then the algorithm determines if sufficient time has passed, for example 1.5 sec (Step 39), and if not, loops to obtain another signal (Step 40). If sufficient time has passed, the algorithm decreases $I_{st}$, resets $I_{LED}$ to zero (Step 42), and loops for another value (Step 40).

Similarly, if $V_{out}$ is greater than a maximum threshold, the algorithm determines if $I_{LED}$ can be decreased (Step 44). If it can, then the algorithm will decrease $I_{LED}$ (Step 48) and wait for the next sample (Step 40). If $I_{LED}$ is already at a minimum threshold (Step 50), then the algorithm determines if sufficient time has passed (Step 54). If sufficient time has not passed, the algorithm loops for a new value ((Step 40). If sufficient time has passed, the algorithm increases $I_{st}$, resets $I_{LED}$ to zero (Step 58), and loops for the next value (Step 40).

This digitally-assisted analog technique has several advantages. First, compared to the prior art, which in one embodiment was limited to subtracting 3.240 μA, the current invention can subtract large amounts of DC current, because the DRE block can be implemented as a tunable current source.

Figure 2:
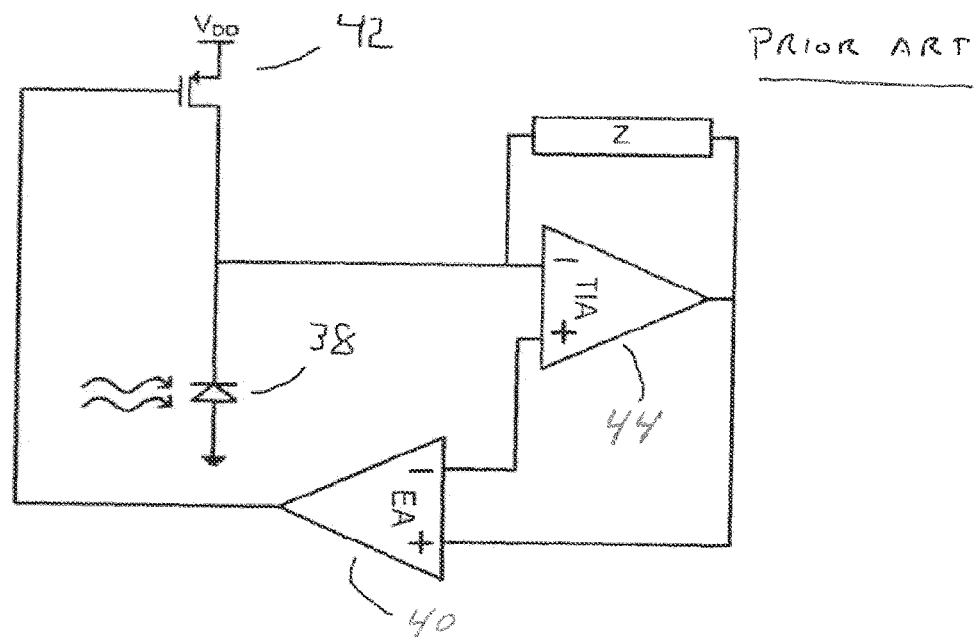
FIG. 2 is a schematic diagram of an embodiment of a dynamic range enhancer (DRE) circuit known to the prior art.

Another advantage to using a digitally assisted analog technique to cancel static current over the analog error amplifier method occurs because the error amplifier 40 (FIG. 2) is trying to maintain the output of the main amplifier 44 (FIG. 2) to a specific voltage value, the error amplifier 40 adds a zero into the frequency domain of the PPG signal at 0.0 Hz. However, the PPG signal band of interest is between 0.1 Hz and 10 Hz, which means that a low frequency pole at 0.1 Hz or below is required to not interfere with the signal bandwidth. This low frequency pole is very difficult to achieve in an integrated circuit chip, and frequently the low frequency pole is higher than 0.1 Hz, reducing the overall gain of the PPG signal. However, when using the present digitally assisted approach, the output of the amplifier is not maintained at a specific voltage, rather it is simply maintained within the rails of the amplifier. Therefore, a zero is not introduced at 0 Hz and the bandwidth of interest is not reduced by the signal chain, allowing for large gains across the entire band of interest.

Still another advantage for using a digitally assisted analog technique is that it is inherently substantially lossless. When using the prior art method shown in FIG. 2, the control is an all-analog loop, so the amount of current subtracted from the photodiode 38 is unknown. However, when using a digitally assisted approach, there are set, specific values of the subtraction current that are controlled by the user. Therefore, the total current (static and time-varying) of the photodiode is known, which, in many instances of PPG, is an important piece of information.

Further, although this circuit is discussed in conjunction with a transducer that produces a large DC component relative to a small AC component, it is also possible to use the circuit and technique with a transducer that produces only DC signals. In such a case, the technique can be used to remove a portion of the DC component to thereby improve the resolution of subsequent A/D conversion.

Figure 5:
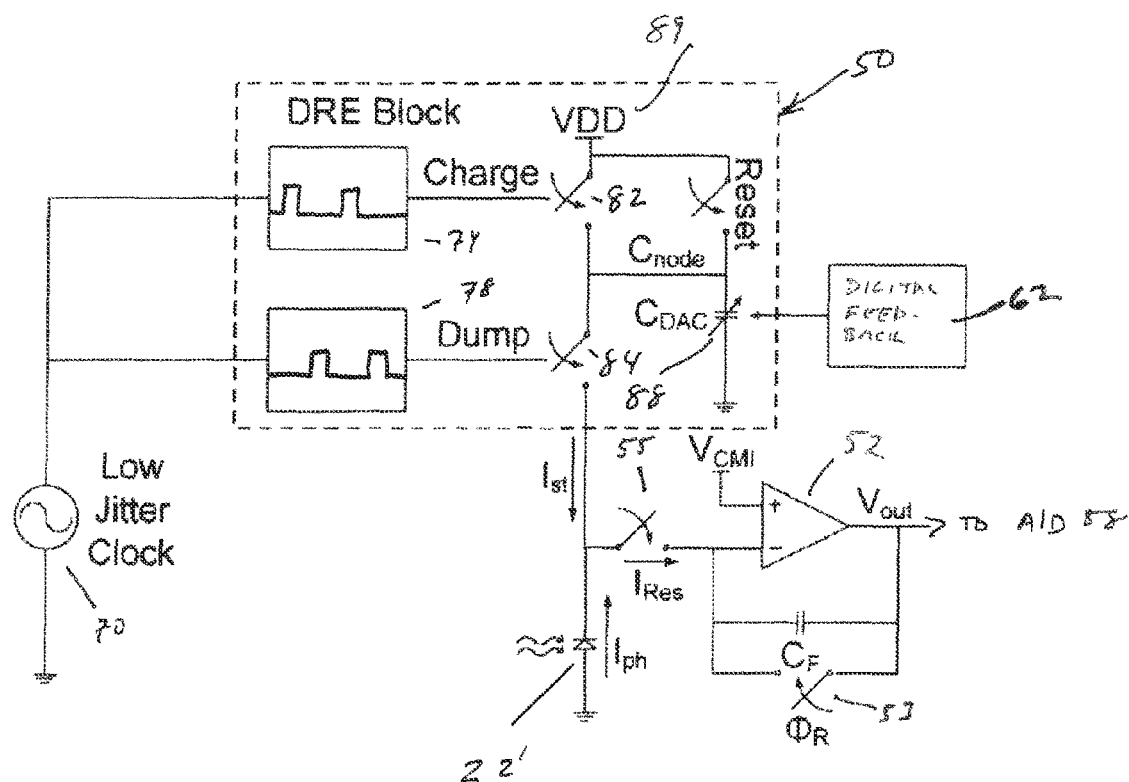
FIG. 5 is a schematic diagram of an embodiment of the DRE circuit of the invention.

In more detail, the dynamic range enhancer, in one embodiment, is an 8-bit switched capacitor current source constructed to generate 100 μA of current. Referring to FIG. 5, in one embodiment, the DRE 50 has one input that is connected to a system clock 70 which is used by the DRE 50 to form two non-overlapping clock signals 74, 78. Each signal is used to open and close a respective switch 82, 84. One terminal of the first switch 82 is connected to a supply voltage 89. The other terminal of the first switch 82 is connected to one terminal of a variable capacitor 88. The capacitance of the variable capacitor 88 is controlled by the digital feedback module 62. The other terminal of the variable capacitor 88 is connected to ground.

The second terminal of the second switch 84 is connected to one terminal of the photodiode 22' and one terminal of the amplifier 52 through switch 55'. The two non-overlapping clock pulses 74 and 78 alternately open and close switches 82 and 84 so as to alternately charge and discharge the variable capacitor 88.

When the system clock 70 operates at 6 MHz, the least significant bit (LSB) of variable capacitor 88 has a value of 73 fF. The voltage source, $V_{DD}$ 89, is 1.8V and the voltage at the cathode of the photodiode 22' is set by the integrating amplifier 52 virtual ground to equal 0.9V. The Charge 82 and Dump 84 switches are both 25 μm/0.18 μm line widths to reduce the RC time constant between the switch resistance and the capacitance of variable capacitor 88. This ensures that the variable capacitor completely charges and discharges for all values of the variable capacitor 88.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes, and not as construction drawings. Omitted details and modifications or alternative embodiments are within the purview of persons of ordinary skill in the art.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A circuit for expanding a dynamic range comprising:
    a transducer generating a signal current on an output terminal in response to a physical quantity, the signal current comprising an AC current and a DC current;
    a dynamic range enhancement circuit having a digital control signal input terminal and producing a variable opposition current at an output terminal in response to a digital signal applied to the digital control signal input terminal, the output terminal of the dynamic range enhancement circuit being in electrical communication with the transducer output terminal;
    a transimpedance amplifier having a input terminal and an output terminal, the input terminal of the transimpendnce amplifier in electrical communication with the output terminal of the dynamic range enhancement circuit and the transducer output terminal;
    an analog to digital converter having an input terminal in electrical communication with the output terminal of the transimpedance amplifier and having an output terminal; and
    a digital feedback circuit having an input terminal in electrical communication with the output terminal of the analog to digital converter and having an output terminal in electrical communication with the digital control signal input terminal of the dynamic range enhancement circuit,
    wherein the opposition current from the dynamic range enhancement circuit is set substantially equal to the DC current portion of the signal current from the transducer by the digital feedback circuit in response to the difference between DC current portion of the signal current and the opposition current.

2. The circuit of claim 1 wherein the transimpedance amplifier is configured as a switched integrator.

3. The circuit of claim 1 wherein the transimpedance amplifier is configured as a resistive transimpedance amplifier.

4. The circuit of claim 1 wherein the transducer is a photodetector.

5. The circuit of claim 4 wherein the transducer is a photodiode.

6. A photoplethysmograph circuit with an expanded dynamic range comprising:
  a receiver portion comprising:
    a transducer generating a signal current on an output terminal in response to a physical quantity, the signal current comprising an AC current and a DC current;
    a dynamic range enhancement circuit having a digital control signal input terminal and producing a variable opposition current at an output terminal in response to a digital signal applied to the digital control signal input terminal, the output terminal of the dynamic range enhancement circuit being in electrical communication with the transducer output terminal;
    a transimpedance amplifier having an input terminal and an output terminal, the input terminal of the transimpedance amplifier in electrical communication with the output terminal of the dynamic range enhancement circuit and the transducer output terminal;
    an analog to digital converter having an input terminal in electrical communication with the output terminal of the transimpedance amplifier and having an output terminal; and
    a first digital feedback circuit having an input terminal in electrical communication with the output terminal of the analog to digital converter and having an output terminal in electrical communication with the digital control signal input terminal of the dynamic range enhancement circuit,
    wherein the opposition current from the dynamic range enhancement circuit is set substantially equal to the DC current portion of the signal current from the transducer by the first digital feedback circuit in response to the difference between DC current portion of the signal current and the opposition current; and
  a light source module comprising:
    one or more light sources each with a different wavelength; and
    an intensity control in electrical communication with each light source,
    wherein the intensity control is adjusted to pulse each light source; and
    wherein each light source is positioned such that light transmitted from the light source is received by the transducer.

7. The photoplethysmograph circuit of claim 6 wherein the transimpedance amplifier is configured as a switched integrator.

8. The photoplethysmograph circuit of claim 6 wherein the transimpedance amplifier is configured as a resistive transimpedance amplifier.

9. The photoplethysmograph circuit of claim 6 wherein the transducer is a photodetector.

10. The photoplethysmograph circuit of claim 9 wherein the photodetector is a photodiode.

11. The photoplethysmograph circuit of claim 6 wherein each of the light sources is a respective light emitting diode.

12. The photoplethysmograph circuit of claim 6 wherein the light received by the transducer from the light source is light transmitted through bodily tissue.

13. The photoplethysmograph circuit of claim 6 wherein the light received by the transducer from the light source is light reflected by bodily tissue.

14. The photoplethysmograph circuit of claim 6 wherein the intensity control comprises:
  a respective driver for each light source; and
  a second digital feedback circuit having an input terminal in electrical communication with the output terminal of the analog to digital converter and having an output terminal in electrical communication with each of the drivers.

15. The photoplethysmograph circuit of claim 6 wherein the output terminal of the A/D converter is in communication with the input terminal of a decimator.

16. The photoplethysmograph circuit of claim 6 wherein the decimator has an output terminal in communication with a serial dataout circuit.

17. The photoplethysmograph circuit of claim 6 wherein the intensity control comprises an independent intensity controller for each respective LED.

18. A dynamic range enhancement circuit comprising:
  a clock;
  a DRE clock circuit generating two non-overlapping clock output signals;
  a variable capacitor having a ground terminal in electrical communication with ground, a control terminal which controls the capacitance of the variable capacitor, and an input terminal;
  a first switch, comprising an input terminal in communication with a voltage source, a control terminal in electrical communication with one of the non-overlapping clock output signals, and an output terminal in electrical communication with the input terminal of the variable capacitor;
  a second switch, comprising an output terminal, a control terminal in electrical communication with the other of the non-overlapping clock output signals, and an input terminal in electrical communication with the output terminal of the first switch and in electrical communication with the input terminal of the variable capacitor,
  wherein the first clock signal causes the first switch to connect the input terminal of the variable capacitor to the voltage source, and
  wherein the second clock signal causes the second switch to connect the input terminal of the variable capacitor to a current sink.

19. The dynamic range enhancement circuit of claim 18 wherein the variable capacitor is controlled by a digital feedback unit.

* * * * *